(12) United States Patent
Mamadov et al.

(10) Patent No.: US 8,158,837 B2
(45) Date of Patent: Apr. 17, 2012

(54) METHOD FOR SELECTIVE HYDROGENATION OF ACETYLENE TO ETHYLENE

(75) Inventors: Agaddin Mamadov, Houston, TX (US); Saeed Al-Wahabi, Riyadh (SA); Akram Al-Alwan, Riyadh (SA)

(73) Assignee: Saudi Basic Industries Corporation, Riyadh (SA)

(*) Notice: Subject to any disclaimer, the term of this patent is extended or adjusted under 35 U.S.C. 154(b) by 920 days.

(21) Appl. No.: 11/887,992

(22) PCT Filed: Apr. 6, 2006

(86) PCT No.: PCT/EA2006/000003
§ 371 (c)(1),
(2), (4) Date: Oct. 5, 2007

(87) PCT Pub. No.: WO2006/105799
PCT Pub. Date: Oct. 12, 2006

(65) Prior Publication Data
US 2009/0326288 A1    Dec. 31, 2009

(30) Foreign Application Priority Data
Apr. 6, 2005   (EP) .................................... 05007545

(51) Int. Cl.
*C07C 5/08* (2006.01)
(52) U.S. Cl. ........ 585/275; 585/250; 585/259; 585/260; 585/262
(58) Field of Classification Search .................. None
See application file for complete search history.

(56) References Cited

U.S. PATENT DOCUMENTS

| | | | |
|---|---|---|---|
| 2,723,299 A | 11/1955 | Manzo et al. | |
| 4,009,219 A | 2/1977 | Tamers | |
| 4,128,595 A | 12/1978 | Montgomery | |
| 4,227,025 A | 10/1980 | Montgomery | |
| 4,571,442 A | 2/1986 | Cosyns et al. | |
| 4,585,897 A | 4/1986 | Fields et al. | |
| 4,906,800 A | 3/1990 | Henry et al. | |
| 4,982,032 A | 1/1991 | Winzenburg et al. | |
| 5,118,893 A | 6/1992 | Timmons et al. | |
| 6,350,717 B1 | 2/2002 | Frenzel et al. | |
| 7,045,670 B2 * | 5/2006 | Johnson et al. | 585/259 |
| 2005/0048658 A1 * | 3/2005 | Johnson et al. | 436/37 |
| 2006/0217579 A1 * | 9/2006 | Bailey | 585/259 |

FOREIGN PATENT DOCUMENTS

WO    WO03/106020    12/2003

OTHER PUBLICATIONS

"Studies on the Selective Hydrogention of Acetylene", Chen et al., Database CA[Online] Chemical Abstracts Service, STN Database, Abstract.
"Selective Hydrogenation of Ethyne on .gamma.-Mo2N", Hao et al., Database CA[Online] Chemical Abstracts Service, STN Database, Abstract.
"Optimization of the Acetylene Selective Hydrogenation Unit at Ethylene Production Plant", Castillo et al., Database CA[Online] Chemical Abstracts Service, STN Database, Abst.
European Search Report; European Application No. 05007545.6; Date of Mailing: Mar. 1, 2006; 14 Pages.
International Search Report; International Application Number PCT/EA2006/000003; International Filing Date Apr. 6, 2006; Date of Mailing Sep. 25, 2006; 5 pages.
Written Opinion of the International Searching Authority; International Application No. PCT/EA2006/000003; International Filing Date Apr. 6, 2006; Date of Mailing Sep. 25, 2006; 10 pages.

* cited by examiner

*Primary Examiner* — Tam M Nguyen
(74) *Attorney, Agent, or Firm* — Cantor Colburn LLP

(57) ABSTRACT

The present invention relates to a method for selective hydrogenation of acetylene to ethylene, comprising the steps of: i) introducing a feed comprising acetylene and hydrogen into a reactor containing a supported catalyst, wherein the reactor is a fixed bed reactor containing the supported catalyst additionally diluted with a solid diluent, or the reactor being a wash coated reactor wherein the supported catalyst is coated on reactor walls; and ii) hydrogenating of acetylene to ethylene in the presence of the supported catalyst.

11 Claims, No Drawings

METHOD FOR SELECTIVE HYDROGENATION OF ACETYLENE TO ETHYLENE

FIELD OF THE INVENTION

The present invention relates to a method for selective hydrogenation of acetylene to ethylene.

BACKGROUND ART

The hydrogenation of acetylene in industrial scale is typically used for purification of ethylene produced by ethane stream cracking from small amounts (0.5-0.9 mol-%) of acetylene.

U.S. Pat. No. 4,585,897 discloses a process for hydration and condensation of acetylene in a crude acetylene stream containing water in the presence of a zirconia-alumina catalyst containing water.

U.S. Pat. No. 2,723,299 discloses a process for preparing styrene and benzene by heating a mixture of acetylene and monovinyl acetylene to a specific temperature under a specific pressure in the presence of a nickel-based catalyst.

U.S. Pat. No. 4,009,219 discloses a process of producing benzene wherein lithium carbide which has been produced is hydrolysed to produce acetylene which is subsequently cyclysized to produce benzene.

Further, U.S. Pat. No. 4,982,032 discloses a process for the conversion of a wet acetylene-containing stream to a product rich in the aromatics benzene, toluene and xylene, wherein the acetylene-containing stream is contacted with a promoted catalyst composition comprising a minor amount of zinc ion incorporated in a major amount of a borosilicate molecular sieve composited in an inorganic matrix.

U.S. Pat. No. 4,227,025 discloses a process for the effective removal of acetylene from a first gas feed which comprises feeding said gas together with hydrogen at an acetylene removal temperature in contact with a noble metal hydrogenation catalyst.

U.S. Pat. No. 4,227,025 discloses in detail the hydrogenation of acetylene in ethylene-containing mixture for purification of ethylene from about 2.200 ppm of acetylene in the presence of a catalyst of Pd supported on $Al_2O_3$.

Further, U.S. Pat. No. 4,128,595 discloses a process for the selective hydrogenation of acetylenic compounds in the liquid phase which comprises contacting hydrogen and a gaseous hydrocarbon stream containing acetylene with a supported catalyst comprising a group VIII metal under hydrogenation conditions.

Up to now, Pd based industrial catalysts on a support can operate only at low concentrations of acetylene (0.5-0.9 mol-%), and even at these concentrations the catalyst deactivates because of the formation of heavy hydrocarbons, which are called green oil. Therefore, for such processes deep hydrogenation reactions are characteristic, which lead to the loss of ethylene.

The typical gas compositions from methane pyrolysis step contain 8-10 wt.-% acetylene, and the existing catalyst systems cannot work in the presence of this amount of acetylene due to the very fast deactivation of the catalyst by formation of coke fragments. Therefore, traditional catalytic acetylene hydrogenation has the following disadvantages:

Acetylene hydrogenation to ethylene is used only for purification of ethylene from small amounts of acetylene. These methods cannot be used for hydrogenation of high amounts of acetylene for production of ethylene.

Traditional processes of gas phase purification of ethylene from acetylene hydrogenation lead to the loss of some ethylene because of low selectivity of these catalysts.

During traditional gas phase acetylene hydrogenation on Pd-based catalysts the formation of green oil on the surface of catalysts takes place leading to the deactivation of the catalyst.

The traditional gas phase hydrogenation processes are limited with regard to the ratio of hydrogen to acetylene which has to be controlled specifically for keeping a high selectivity of ethylene.

The traditional gas phase hydrogenation processes require the specific control of the reaction temperature, run away of the temperature leads to a sharp decrease of selectivity.

Further, traditional gas phase hydrogenation processes require the specific control of the amount of carbon monoxide in the feed; without the addition of carbon monoxide the selectivity of ethylene is low, whereas at high concentrations of carbon monoxide, for example more than about 1.200 ppm, the conversion of acetylene decreases almost to zero due to the strong adsorption of carbon monoxide.

Due to these problems, it is very difficult to realize the hydrogenation of acetylene at high concentrations for production of ethylene from acetylene.

U.S. Pat. No. 5,118,893 discloses a catalytic conversion of acetylene in the presence of nickel or cobalt-containing zeolite catalyst with the addition of hydrogen to the acetylene feed. It was observed that acetylene conversion in the presence of zeolite-containing catalyst leads to the rapid deactivation of catalyst due to very fast polymerization of acetylene on the surface of the catalyst.

It was reported that with the increase of acetylene concentration in the mixture deactivation of catalyst proceeds very fast.

SUMMARY OF THE INVENTION

It is therefore an object of the present invention to provide a method for selective hydrogenation of acetylene to ethylene which overcomes the drawbacks of the prior art, especially to provide a method which enables the production of ethylene with high conversion of acetylene and high selectivity of ethylene, utilizing increased acetylene concentrations in the feed.

This object is achieved by a method for selective hydrogenation of acetylene to ethylene, comprising the steps of: i) introducing a feed comprising acetylene and hydrogen into a reactor containing a supported catalyst, wherein the reactor is a fixed bed reactor containing the supported catalyst additionally diluted with a solid diluent, or the reactor being a wash coated reactor wherein the supported catalyst is coated on reactor walls; and ii) hydrogenating of acetylene to ethylene in the presence of the supported catalyst.

Preferably, the catalyst is selected from group VIII of the periodic system of elements, preferably palladium.

Moreover the feed may be obtained from thermal pyrolysis of methane.

In one embodiment, the amount of acetylene in the feed is from about 0.1 to about 20 wt.-%, preferably from about 8 to about 20 wt.-%, preferably from about 10 to about 15 wt.-%, based on the total weight of the feed.

Preferably, the method is carried out at a temperature of about 30 to about 500° C., preferably about 40 to about 230° C.

Conveniently, the method is carried out at a space velocity of about 1.000 to about 2.000.000 h$^{-1}$, preferably about 2.500-170.000$^{-1}$.

Preferably, the support is $SiO_2$, $ZrO_2$, $Al_2O_3$, $TiO_2$, or a mixture thereof.

More preferably, the diluent is $SiO_2$, $ZrO_2$, $Al_2O_3$, $TiO_2$ or a mixture thereof.

Most preferably, the molar ratio of hydrogen to acetylene in the feed is from about 5 to about 10, preferably from about 6 to about 7.

The feed may additionally comprise methane, carbon monoxide, nitrogen, carbon dioxide, water, or liquid hydrocarbons, or mixtures thereof.

In one embodiment, the reactor is a quartz, ceramic or metallic reactor.

Preferably, the reactor wall comprises metal gauze or metal mesh. Then, any shape can be used for that gauze or mesh, also resulting in a high surface area.

The flow rate of the feed may be from about 100 to about 1.000 cm$^3$/min.

Preferably, the molar ratio of support to catalyst is from about 80 to about 1.000, more preferably from about 90 to about 200 and the particle size of the supported catalyst is from about 45 to about 60 mesh.

Even preferred, the method is carried out in gas or liquid phase and may be carried out under isothermal or non-isothermal conditions and a pressure of about 1 to about 25 bar.

More preferred, the supported catalyst is additionally modified with one of the elements selected from the group consisting of Cu, Co, Cr, K, Pt, Ru, Au, Ag or mixtures thereof.

In one embodiment, the supported catalyst has been reduced with hydrogen for 1-48, preferably 2-20 hours, prior to employment.

Further, the internal diameter of the reactor may be from about 4 to about 45 mm, preferably from about 4 to about 25 mm.

Finally, it is preferred that the weight ratio of diluent to supported catalyst is from about 200 to about 1, preferably from about 50 to about 170.

Surprisingly, it was found that with the method of the present invention acetylene may be converted into ethylene at high concentrations with high conversion and high selectivity. In detail, acetylene concentrations of more than about 10 wt.-% may be utilized. A feed-containing acetylene concentration of about 10 wt.-% may be obtained from thermal pyrolysis of methane. The yield of ethylene in the inventive method is very high, about 80%.

It was found that it is difficult with the traditional fixed bed catalyst to keep high selectivity of ethylene due to the high exothermity of the reaction and runaway of the temperature inside of the catalyst bed. Therefore, the present invention utilizes a specific loading of the catalyst in the reaction zone and a specific shape design of the catalyst which eliminates the dehydrogenation of ethylene to ethane through effective way of heat transfer. This is achieved by the first alternative of the inventive process, wherein a supported catalyst is used in a fixed bed reactor wherein the supported catalyst is additionally diluted with a solid diluent. Further, this is achieved by the second alternative of the inventive method wherein the reactor has been wash coated and the supported catalyst is coated on reactor walls. In the first alternative, the dilution contributes to the dissipation of the reaction heat in long diluted catalyst beds. In the approach with the wash coated reactor, it is quite easy to remove the heat produced during the reaction on the reactor wall.

Further, it was surprisingly found that the acetylene hydrogenation catalyst should have a low concentration of catalyst on the support which is necessary for high selectivity. For the supported catalyst used in the inventive method it was found that palladium supported on $TiO_2$ was most effective.

Palladium dispersed in such a diluted catalyst system allows to produce a stable catalyst with complete conversion of acetylene at high ethylene selectivity.

The supported catalyst used in the inventive method may be prepared according to any method of catalyst deposition on a support, such as chemical vapor deposition, coating with traditional impregnation methods, deposition by electrochemical methods, such as a method of electrophoresis deposition.

The inventive method may be carried out at very high ratios of hydrogen to acetylene without consecutive ethylene conversion reactions and selectivity decrease. In the inventive method no formation of a green oil and oligomer productions because of the specific reaction performance is observed.

One further advantage of the inventive method is the high selectivity for ethylene over the relatively wide temperature range and high selectivity over a wide range of acetylene conversion and concentration. It is assumed that the inventive method realizes an easy desorption of ethylene from the catalyst surface.

Additionally, a preferred parameter to improve the selectivity and catalyst stability is the temperature of the catalyst pretreatment with hydrogen. Preferably, the catalyst is reduced with hydrogen in isothermal or non-isothermal condition in a temperature range of 150-500° C. with a pretreatment duration of 1-24 hours.

Further, the heat release from the reaction zone can be easily achieved by the inventive method. Especially, in the case of high space velocity conditions there is effective recovery of the reaction heat and an effective dissipation through the catalyst bed is achieved.

Due to the high ratio of hydrogen to acetylene it is assumed that the formation of green oil and heavy hydrocarbons will be very low.

The productivity of the inventive method can be increased even to 2.000.000 cm$^3$/g.h, which is significantly increased compared to the productivities given in the literature.

The hydrogenation is carried out without accumulation of coke fragments.

The effect of carbon monoxide to catalyst activity is not significant for the inventive method.

The contact time in the inventive method can be the same as in short residence time pyrolysis process which make the integration of these processes possible, that is as a result a process for conversion of methane to ethylene via pyrolysis of methane to acetylene, followed by hydrogenation of acetylene to ethylene.

Additional advantages and features of the present invention will become apparent from the following examples section, which examples are not considered to limit the scope of the invention.

DESCRIPTION OF THE PREFERRED EMBODIMENT

Experimental

Catalyst Preparation

The necessary amount of support, such as $TiO_2$, $SiO_2$, has been prepared in the form of a gel or a dense suspension. The support was then promoted by palladium by ion adsorption method, from organic or inorganic salts, such as $Pd(NO_3)_2$ or $PdCl_2$, or compositions, such as $Pd(NH_3)_4(OH)_2$. The supported catalyst was dried at 120° C. and was then crushed to a particle size of 40-60 mesh and was, if desired, diluted with quartz particles of the same size and was finally reduced by hydrogen for one hour before the reaction.

The thus obtained diluted and supported catalyst was used in a fixed bed reactor. On the other hand, the supported (and undiluted) catalyst was utilized to prepare the wash coated reactor as follows:

The internal reactor walls, having, e.g., an internal diameter of ¼ or ⅛ inch were washed three times from top to the bottom of the reactor inside a hot furnace at 250° C. with a suspension of $TiO_2$. The concentration of $TiO_2$ in the suspension was about 2% by weight. After drying, the reactor was then washed three times with a solution of $Pd(NO_3)_2$. The amount of palladium relative to $TiO_2$ was about 0.8% by weight.

An EM analysis showed the presence of Ti on the wall with 10% relative to the internal wall surface. Palladium could not be detected due to the low concentration thereof. The reactor was, after washing, treated with hydrogen at 400° C. for one hour, before the hydrogenation process was started.

The reaction conditions and process parameters are illustrated in the following examples.

Example 1

A method according to the present invention was carried out in a metallic reactor having an internal diameter of 4 mm using a mixture of 10% $C_2H_2$+20% $CH_4$+60% $H_2$ and 10% $CO_2$. The catalyst provided in the reactor has been treated with hydrogen at 350° C. for 2 hours and then the mixture was fed into the reactor with a flow rate of 120 cm³/min at a temperature of 230° C. The reactor was kept at non-isothermal conditions and had a temperature profile of 230° C. at the inlet side and 90° C. at the outlet side of the reactor. The pressure in the reactor was atmospheric.

After reduction of the catalyst with hydrogen at 350° C., at this temperature full conversion of acetylene was observed, but selectivity to ethane was very high. Cooling of the reactor to 60° C. increased the selectivity to ethylene and even at this low temperature full conversion of acetylene was observed. To achieve high stable selectivity to ethylene with very high conversion of acetylene, the temperature of the reactor was kept in the range of 150-198° C. The reaction products of acetylene hydrogenation are $C_2H_4$, $C_2H_6$ and $CH_4$.

The following table 1 illustrates the process parameters obtained in metallic reactor with 4 mm I.D. All data shown in the following tables are given in mol-%.

In example 1, the conversion of acetylene in catalyst assisted 4 mm I.D. metallic wash coated reactor in the presence of carbon dioxide is shown; flow rate: 120 cm³/min; feed composition: 10% $C_2H_2$+60% $H_2$+20% $C_4$+10% $CO_2$; temperature: 198° C.

TABLE 1

| Time, Hours | 6 | 21 | 44 | 74 |
|---|---|---|---|---|
| $C_2H_2$ conversion, % | 97.0 | 95.2 | 93.0 | 90.3 |
| C2H4 concentr. in Outlet gas, % | 8.7 | 8.6 | 8.5 | 8.5 |
| $C_2H_4$ selectivity, % | 84.2 | 85.1 | 86.0 | 88.2 |
| $C_2H_6$ Selectivity % | 7.8 | 6.2 | 5.4 | 3.8 |
| CH4 Selectivity % | 8.0 | 8.7 | 8.6 | 8.0 |

Example 2

In example 2 the conversion of acetylene in a wash coated metallic reactor provided with a catalyst at a flow rate of 120 cm³/min at different temperatures is shown; feed composition: 10% $C_2H_2$+60% $H_2$+30% $CH_4$.

TABLE 2

| Temperature, ° C. | 130 | 188 | 200 |
|---|---|---|---|
| Time, day | 1 | 2 | 3 |
| C2H2 conversion, % mole | 100 | 95.2 | 96.3 |
| C2H4 concentration in outlet gas, % mole | 9.1 | 9.5 | 9.4 |
| C2H4 selectivity, % mole | 84.6 | 90.0 | 91.5 |
| C2H6 selectivity, % mole | 4.8 | 4.5 | 3.1 |
| CH4 selectivity, % mole | 10.6 | 5.5 | 5.4 |

Example 3

In example 3 the effect of the flow rate and temperature to acetylene conversion in a quartz reactor provided with a fixed bed catalyst is shown. Feed composition: 10% $C_2H_2$+60% $H_2$+30% $C_4$, reaction time: 40 hours.

TABLE 3

| Temperature, ° C. | 160 | 200 |
|---|---|---|
| Flow rate, cc/min | 60 | 120 |
| C2H2 conversion, % | 87.0 | 90.2 |
| C2H4 concentration, % | 8.7 | 9.0 |
| C2H4 selectivity, % mole | 86.0 | 85.2 |
| C2H6 selectivity, % | 2.7 | 3.6 |
| CH4 selectivity, % | 11.3 | 11.2 |

Example 4

In example 4 the results of acetylene conversion in a quartz reactor provided with a fixed bed catalyst at 230° C. are given; flow rate: 120 cm³/min; feed composition: 10% $C_2H_2$+60% $H_2$+30% $CH_4$; reaction time: 60 hours.

TABLE 4

| C2H2 conversion, % mole | 96.0 |
|---|---|
| C2H4 concentration in the outlet gas, % | 9.1 |
| C2H4 selectivity, % mole | 86.0 |
| C2H6 selectivity, % mole | 10.2 |
| CH4 selectivity, % mole | 3.9 |

Comparative Example 5

In comparative example 5 the conversion of acetylene in the presence of a fixed bed of 2% $Pd/H_3PO_4$+HZSM-5 catalyst at different temperatures is given: catalyst: 0.4 mg.

TABLE 5

| Temperature ° C. | 300 | 350 | 400 | 500 |
|---|---|---|---|---|
| Feed total flow rate, cc/mm | 10 | 10 | 10 | 3 |
| $C_2H_2$ conversion, % | 27.4 | 47.3 | 57.1 | 45 |
| $C_2H_4$ selectivity, % mole | 2.2 | 5.2 | 5.5 | 5.3 |

Example 6

In example 6 the results of acetylene conversion in a quartz reactor provided with a fixed bed catalyst at 60° C. are given;

flow rate: 500 cm³/min; catalyst: 0.02 g; feed composition: 10% $C_2H_2$+60% $H_2$+30% $CH_4$; reaction time: 60 hours.

TABLE 6

| | |
|---|---|
| C2H2 conversion, % mole | 90.0 |
| C2H4 concentration in the outlet gas, % | 8.7 |
| C2H4 selectivity, % mole | 89.2 |
| C2H6 selectivity, % mole | 4.2 |
| CH4 selectivity, % mole | 6.6 |

Example 7

In example 7 the results of acetylene conversion in a metallic reactor provided with the fixed bed catalyst (Pd-containing catalyst modified with Ag) at 199° C. are given; flow rate: 200 cm³/min; feed composition: 9% $C_2H_2$+61% $H_2$+30% $CH_4$; reaction time: 60 hours.

TABLE 7

| | |
|---|---|
| C2H2 conversion, % mole | 91.5 |
| C2H4 concentration in the outlet gas, % | 8.45 |
| C2H4 selectivity, % mole | 90.0 |
| C2H6 selectivity, % mole | 5.8 |
| CH4 selectivity, % mole | 4.2 |

Example 8

In example 8, the results of acetylene conversion in a fixed bed reactor are given, filled with glass cylinders, (3 mm ID, 6 mm length), coated with catalyst material and reduced with hydrogen at 380° C. Flow rate 100 cm³/min; feed composition: 11.9% $C_2H_2$+64.9% $H_2$+23.2% $N_2$.

TABLE 8

| | |
|---|---|
| C2H2 conversion, % mole | 97.7 |
| C2H4 concentration in the outlet gas, % | 11.06 |
| C2H4 selectivity, % mole | 82.6 |
| C2H6 selectivity, % mole | 1.7 |
| CH4 + heavy hydroc. selectivity, % mole | 15.7 |
| C2H4 yield, % mole | 80.7 |

Example 9

0.12 g metal gauze with more than 65 mesh was used as a support and impregnated with $TiO_2$ with 30% relative to the weight of qauze. After drying the obtained material, it was impregnated with $Pd(NO_3)_2$, dried and reduced with hydrogen for one hour at 400° C., whereupon the hydrogenation reaction was started. Flow rate of the mixture is 400 cm³/min; gas composition: 20.26% $C_2H_2$, 20.27% $N_2$, 59% $H_2$.

TABLE 9

| | |
|---|---|
| C2H2 conversion, % mole | 100 |
| C2H4 concentration in outlet gas, % | 19.57 |
| C2H4 selectivity, % mole | 86.5 |
| C2H6 selectivity, % mole | 6.5 |
| CH4 + heavy hydrocarbon selectivity, % mole | 7 |

According to the present invention, the method may be carried out in the presence of a supported catalyst prepared by coating any shape of quartz or ceramic particles, glass cylinders or metal gauze materials with the supported catalyst.

Example 10

Example 10 demonstrates the performance of a reactor coated with $TiO_2$+Pd+Ag; Ag/Pd=2, 138 cm³/min in the presence of water; gas flow rate 40 cm³/min; temperature 269° C.; water amount 0.04 ml/min or 120 cm³/min at reaction conditions; gas composition: 12.5% $C_2H_2$+27.5% $N_2$+60% $H_2$.

TABLE 10

| | |
|---|---|
| C2H2 conversion, % mole | 99 |
| C2H4 concentration in outlet gas, % | 12 |
| C2H4 selectivity, % mole | 87.8 |
| C2H6 selectivity, % mole | 1.5 |
| CH4 + heavy hydrocarbon selectivity, % mole | 11.7 |

As can be seen from the above examples, the conversion of acetylene in the inventive method is stable after 140 hours, and the catalyst in the inventive method is much more stable in comparison to methods of the prior art, where acetylene conversion and ethylene selectivity decreases from the beginning of the reaction.

In case of high acetylene concentrations, the catalyst is stable for 14 days without formation of any coke fragments and activity decrease. In any case of catalyst deactivation during long time screening activity can be restored by treatment consequently with air and hydrogen. During treatment of the catalysts with air there was not observed formation of any amount of carbon monoxide or carbon dioxide.

The features disclosed in the foregoing description or in the claims may, both separately and in any combination thereof, be material for realizing the invention in diverse forms thereof.

The invention claimed is:

1. A method for selective hydrogenation of acetylene to ethylene, comprising the steps of:
   i) introducing a feed comprising acetylene and hydrogen into a reactor containing a supported catalyst, and
   ii) hydrogenating acetylene to ethylene in the presence of the supported catalyst;
   wherein the reactor is a fixed bed reactor containing the supported catalyst additionally diluted with a solid diluent in a weight ratio of diluent to supported catalyst of from 50 to 170,
   wherein the amount of acetylene in the feed is more than 10 wt.-%, based on the total weight of the feed.

2. The method according to claim 1, wherein the catalyst is selected from group VIII of the periodic system of elements.

3. The method according to claim 1, wherein the catalyst is palladium.

4. The method according to claim 1, wherein the feed is obtained from thermal pyrolysis of methane.

5. The method according to claim 1, wherein the method is carried out at a temperature of from 40 to 230° C., and at a pressure of 1 to 25 bar.

6. The method according to claim 1, wherein the support is selected from the group consisting of $SO_2$, $ZrO_2$, $Al_2O_3$, $TiO_2$, or mixtures thereof.

7. The method according to claim 1, wherein the diluent is selected from the group consisting of $SiO_2$, $ZrO_2$, $Al_2O_3$, $TiO_2$, or mixtures thereof.

8. The method according to claim 1, wherein the hydrogen and acetylene in the feed are in a molar ratio of hydrogen to acetylene from 5 to 10.

9. The method according to claim 1, wherein the feed additionally comprises methane, carbon monoxide, nitrogen, carbon dioxide, water, liquid hydrocarbons, or mixtures thereof.

10. The method according to claim 1, wherein the supported catalyst is additionally modified with one of the elements selected from the group consisting of Cu, Co, Cr, K, Pt, Ru, Au, Ag, or mixtures thereof.

11. The method according to claim 1, wherein the supported catalyst has been reduced with hydrogen for 2-20 hours, prior to employment.

\* \* \* \* \*